Sept. 24, 1957 H. A. M. VERSCHUREN Plant Pat. 1,641
ROSE PLANT
Filed Dec. 31, 1956
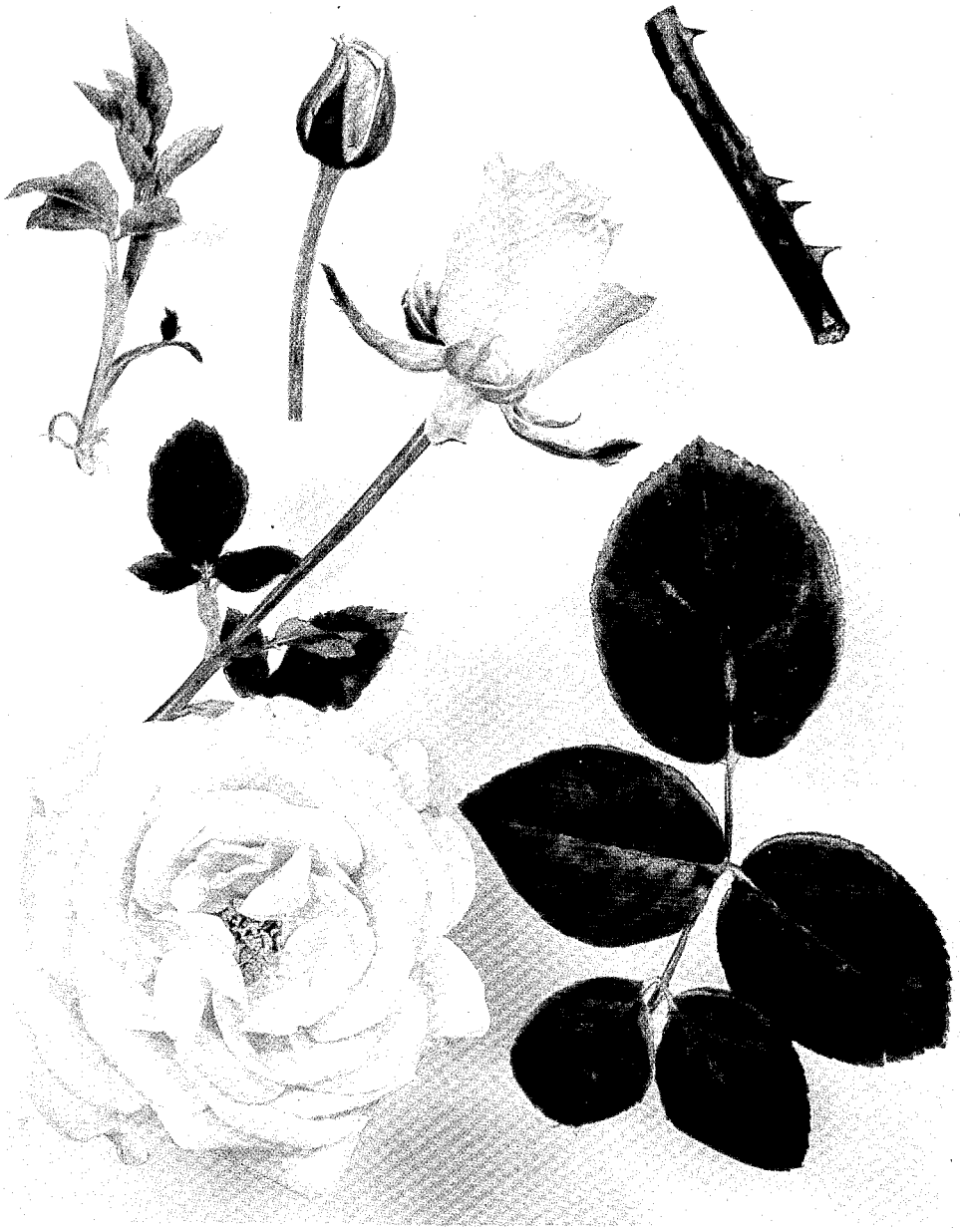
Inventor.
H. A. M. Verschuren
By: Robb & Robb
Attorneys.

United States Patent Office

Plant Pat. 1,641

Patented Sept. 24, 1957

1,641

ROSE PLANT

Hendrikus Antonie Maria Verschuren, Haps, Netherlands, assignor to Jackson & Perkins Company, Newark, N. Y., a corporation of New York Application December 31, 1956, Serial No. 631,986

1 Claim. (Cl. 47—61)

The present invention relates to a new and distinct variety of rose plant of the hybrid tea class, which was originated by me by crossing the variety "Peace" (U. S. Plant Patent No. 591) with the variety "Dame Edith Helen" (unpatented).

The primary objective of this cross was to produce a new rose variety having the plant habit and form of the very popular variety "Peace," but bearing flowers of a color different from those of this parent. To this end, the parent variety "Peace" was crossed with the large, full-cupped, light pink rose known as "Dame Edith Helen," which resulted in fully achieving the desired objective, as evidenced by the following characteristics which distinguish the new variety from its parents, as well as from all other varieties of which I am aware, when such characteristics are considered as a whole:

(1) An upright, vigorous growth and foliage generally similar to "Peace";

(2) Large, cupped blooms which have slowly opening centers; and (3) A distinctive Thulite Pink, lightly overcast with Cameo Pink, general color tonality of the blooms which are much more colorful than those of "Peace."

Asexual reproduction of the new variety by budding, as performed at Newark, New York, U. S. A., and also at Pleasanton, California, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
- *Seed parent.*—"Peace."
- *Pollen parent.*—"Dame Edith Helen."

Classification:
- *Botanic.*—Hybrid tea.
- *Commercial.*—Hybrid tea.

*Flower*

(Observations made from specimens grown outdoors at Newark, New York, U. S. A., in the late morning and near the middle of July.)

Blooming habit: Recurrent—continuous.

Bud:
- *Size.*—Large
- *Form.*—Ovoid; is not affected by wet or hot weather.
- *Color.*—When sepals first divide—Spinel Red, Plate 26. When petals begin to unfurl—Spinel Pink, plate 26. When half-blown: inside of petals—Center of petal Cameo Pink, Plate 26, with outer edge of petal Thulite Pink, Plate 26, lightly overcast with Cameo Pink, Plate 26; reverse of petals—Center of petal La France Pink, Plate 1, with outer edge of petal overcast with Thulite Pink, Plate 26.
- *Sepals.*—Slightly branched; curl back when petals begin to unfurl. Color: inside—Kildare Green, Plate 31; outside—Light Cress Green, Plate 31.
- *Calyx.* — Shape — funnel. Size — small. Aspect — smooth. Odor when rubbed—none. Color—Biscay Green, Plate 17.
- *Peduncle.* — Length — medium. Aspect — smooth. Strength—stiff; heavy. Color—Courge Green, Plate 17.
- *Opening.*—Opens up well; is not affected by adverse weather conditions.

Bloom:
- *Size.*—Large. Average size when fully expanded—4¾ inches.
- *Borne.*—Singly.
- *Stems.*—Medium length; strong.
- *Form (when first open).*—Cupped. Permanence—retains its form to the end, but outer petals curl back.
- *Petalage.*—Double (full but open center). Number of petals under normal conditions—from 45 to 50.
- *Color.*—Center of flower—Spinel Pink, Plate 26, lightly overcast with Thulite Pink, Plate 26. Outer petals—Hermosa Pink, Plate 1, lightly overcast with Thulite Pink, Plate 26. Base of petals (aiglet)—Barium Yellow, Plate 16. Inside of petals—Thulite Pink, Plate 26, lightly overcast with Cameo Pink, Plate 26. Reverse of petals—Cameo Pink, Plate 26. General tonality from a distance—Thulite Pink, Plate 26, lightly overcast with Spinel Pink, Plate 26.
- *Discoloration.*—General tonality at end of first day—Thulite Pink, Plate 26, lightly overcast with Spinel Pink, Plate 26. Second day—Thulite Pink, Plate 26, lightly overcast with Spinel Pink, Plate 26. Third day—Thulite Pink, Plate 26, lightly overcast with Cameo Pink, Plate 26.

Petals:
- *Texture.*—Leathery; is not affected by wet or hot weather.
- *Appearance.*—Inside—satiny. Outside—shiny.
- *Form.*—Oval.
- *Arrangement.*—Imbricated, except for the center of the flower where a few petals are irregular.
- *Petaloids in center.*—Few; large.
- *Persistence.*—Drop off cleanly.
- *Fragrance.*—Strong. Nature—tea (average hybrid tea scent).
- *Lasting quality.*—On the plant—long. As cut flower—long.

*Genital organs*

Stamens, anthers: Large; many; regularly arranged around styles. Color—Deep Chrome, Plate 3.

Stamens, filaments (threads): Medium length. Color—Grenadine Pink, Plate 2.

Pollen: Color—Pale Yellow-Orange, Plate 3.

Styles: Bunched; uneven length; medium length; heavy.

Stigmas: Color—Pale Orange-Yellow, Plate 3.

Ovaries: All enclosed in calyx.

Hips: None.

Seeds: None.

*Plant*

Form: Bush.

Growth: Vigorous; upright; branching.

Foliage: Compound of 5 to 7 leaflets.

*Size.*—Large.

*Quantity.*—Normal.

*Color.*—New foliage: upper side—Oxblood Red, Plate 1; under side—Carmine, Plate 1, with center lightly overcast with Rainette Green, Plate 31. Old foliage: upper side—Cress Green, Plate 31; under side—Light Cress Green, Plate 31.

*Shape.*—Oval.

*Texture.* — Upper side — leathery. Under side — smooth.

*Ribs and veins.*—Ordinary.

*Edge.*—Serrated (saw-toothed).

*Serration.*—Both double and single; small.

*Leaf stem.*—Color—Cress Green, Plate 31. Under side—prickly.

*Stipules.*—Medium length; smooth.

Wood:

*New wood.* — Color — Absinthe Green, Plate 31. Bark—smooth.

*Old wood.* — Color — Varley's Green, Plate 18. Bark—smooth.

Thorns:

*Thorns.*—Quantity: on main stalks from base—ordinary; on laterals from stalk—ordinary. Form—narrow base; medium length; hooked downward. Color (when young)—Indian Lake, Plate 26. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by its upright, vigorous growth and foliage comparable to the variety "Peace" (U. S. Plant Patent No. 591), its large cupped blooms having slowly opening centers, and the distinctive Thulite Pink, lightly overcast with Cameo Pink, general color tonality of its blooms.

No references cited.